United States Patent [19]
Dietrich et al.

[11] Patent Number: 6,025,541
[45] Date of Patent: Feb. 15, 2000

[54] METHOD OF USING AS A SELECTABLE MARKER A NUCLEIC ACID CONTAINING AHAS PROMOTER USEFUL FOR EXPRESSION OF INTRODUCED GENES IN PLANTS

[75] Inventors: Gabriele Dietrich, Bussum, Netherlands; Jane Smith, Belluvue, Wash.; Jianying Peng, Lawrenceville, N.J.

[73] Assignee: American Cyanamid Company, Madison, N.J.

[21] Appl. No.: 08/862,881

[22] Filed: May 23, 1997

Related U.S. Application Data

[62] Division of application No. 08/303,266, Sep. 8, 1994, Pat. No. 5,750,866.

[51] Int. Cl.$^7$ ............................. C12N 15/29; C12N 15/82; A01H 4/00; A01H 5/00
[52] U.S. Cl. ......................... 800/205; 800/200; 536/23.6; 536/24.1; 435/172.3; 435/69.1; 435/320.1; 435/419
[58] Field of Search ...................................... 800/205, 200; 536/23.6, 24.1; 435/172.3, 69.1, 320.1, 419

[56] References Cited

PUBLICATIONS

McElroy, David, Isolation of an Efficient Actin Promoter for Use in Rice Transformation Feb., 1990, The Plant Cell, vol. 2, 163,171.

McElroy, David, Construction of Expression Vectors based on the rise actin1 (Act1) 5' Region for use in Monocot Transformation, Mol. Gen Genet (1991) 231:150–160.

Zhang, W., Analysis of Rice Act 1 5' Region Activity in Transgenic Rice Plants, The Plant Cell, vol. 3, 1155–1165, Nov. 1991.

Christensen, A.H., Maize Polyubiquitin genes: structure, thermal perturbation of expression and transcript splicing, and promoter activity following transfer to protoplasts by electroporation, Plant Molecular Biology 18:675–689, 1992.

Kyozuka, J., Anaerobic induction and tissue–specific expression of maize Adh 1 promoter in transgenicrice plants and their progeny, Mol. Gen Genet (1991) 228:40–48.

Planckaert, F., Transient gene expression after electroporation of protoplasts derived from embryogenic maize callus, Plant Cell Reports (1989) 8:144–147.

McElroy, D., Foreign Gene Expression in Transgenic Cereals, Tibtech, Feb. 1994 vol. 12.

Christensen, A.H., Sequence Analysis and Transcriptional Regulation by Heat Shock of Polyubiquitin Transcripts from Maize, Plant Molecular Biology 12:619–632 (1989).

Reynolds, G.J., cDNA cloning of a tetraubiquitin gene, and expression of ubiquitin–containing transcripts, in aleurone layers of Avena fatua, Plant Molecular Biology, 20:753–758 (1992).

Callis, J., Introns Increase Gene Expression in Cultured Maize Cells, Genes & Development 1:1183–1200 (1987).

*Primary Examiner*—Douglas W. Robinson
*Assistant Examiner*—Thomas Haas
*Attorney, Agent, or Firm*—Gale F. Matthews

[57] ABSTRACT

The present invention is directed to isolated non-coding nucleotide sequences useful as promoters for heterologous gene expression in plants. The present invention is also directed to vectors and plant cells comprising the isolated nucleotide sequences.

AHAS promoters from maize are used to express introduced genes at high levels and in various plant tissues. Promoters from the als1 and als2 genes of maize are cloned and sequenced, and the promoter regions from these genes are then introduced into a plasmid 5' to the reporter gene beta-glucuronidase (GUS). Both promoter fragments are from the XI12 maize line. The als1 promoter fragment is approximately 1400 base pairs long, whereas the als2 promoter fragment contains 829 base pairs.

3 Claims, 8 Drawing Sheets

TCTAGAGAAACTAAACTACTAATAAAAATTATTTTTAGCATATT
TTAGTACTGTNGTTTATATTTNNAAATGATAAAGTTTAACTAAA
AGTGCACCGCTAAACCACCGTAAATCCAAAGAGACCGTAAATCT
CTTCCACGCACTCTGTCGTGTACCAACGTGCTGTGGAAACGCTC
ACGTACCTTTGTGTATTATGTACGGATTCGGGCAACGGACATTT
CGACGTCGGTTTGCCAGTCCNATTCCCATCTGAACCACACATCT
CTGAACAAAAGTAGGGGAGGCGCCCGCGTAGCCCCCTTTCCCAC
AATCCCACTCCGTGCCAGGTGCCACCCTCCCCAAGCCCTCGCGC
CGCTCCGAGACAGCCGCCCGCAACCATGGCCACCGCCGCCACCG
CGGCCGCCGCGCTCACC

FIG. 1

CCGGATTTCCCTGTTGCGGATTGCGGGTGGCAGCCTGGCAGGTG
GGTGCGACCCCGTTTGGATTCCCTTGTCTGGGCCCCTTGTGTCA
GTACCGTCTGTACTCCGATGACATGCACCGTCGTCCACAGTCAA
GTCCAAAATCTCCCCTCTTTTTTTTAACGGAACAGTTCAAAACC
TCCTTGACGCACGCTGTCGTGTACCAGCACTCGGTGGACACCAC
GTTTGTAATCCAGGCCGACACGTCGGTCCCACGTCGACAGGCCC
CACCGTCCGGTCTGTAGCGTGTACGTATTCGGGCGACGGACGTG
TCGTCGTCGTCTTGCGAGTCCCATTCCCATCACCATCTGAGCCA
CACATCCTCTGAACAAAGCAGGGAGGCCTCCACGCACATCCCC
CTTTCTCCACTCCGGTCCGTGGCACCCACCCCAAACCCTCGCGC
CGCCTCCGAGACAGCCGCCGCAACCATGGCCACCGCCGCCGCCG
CGTCTACCGCGCTCACTGGCGCCAC

FIG. 2

```
CTGCAGGTCA ACGGATCACC TATCAACATC CCAGCTAAAA ACAGTAAAAA
GGGGGAAAAC GTGGGTGAGT TGAGTCTGTC TTGTGGAAAA AACGTTTTAG
TTTCTCCTGG AATTAACAAT AAAAACAGTT GAACAAGATT GACTGTTCCT
CCGGGAGGGT TTGGAACATC GTTACAGATG TGAGCGAAAG GTGAGGAAAC
AGAGCGGAGG GCTTGGAGGT GACCTCGGTA GTCGACGCCG GAGTTGAGCT
TGATGACGAC ACCGTACTGG CGTACCAGGC CTAGTAGTGA ACACCGGGCC
TGAAGCTGTC GCCGCCGCTG CTCATCTTGT GGGCTGTGCC CGGTGTCCCT
GTTGCGGATT GCGGGTGGCA GCCTGGCAGG TGGGTGCGAC CCGTTTGGAC
TCCCTGATCT GGGCCCTTTG TGTCAGTACC GTCTGTACTC CGATGACATG
CACACCGTCG TCCACAGTCA AGTCCACAAT CTCCCCTCTT TTTTTAACGG
AATAGTTCAA AATCTCCTTG ACGCACGCTA TCGTGTACCA GCGCTCACTG
GACACCACGT TTGTAATCCA CGCCGACACG TCGGTCCCAC GTCGACAGGC
CCCACCGTCC GGTCTGTAGC GTGTACGTAT TCGGGCGACG GACGTGTCGT
CGTCGTCTTG CGAGTCCCAT TCCCATCACC ATCTGAGCCA CACATCCTCT
GAACAAAAGC AGGGAGGCCT CTACGCACAT CCCCCTTTCT CCCACTCCGT
GTCCGTGGCA CCCACCCCAA ACCCTCGCGC CGCCTCCGAG ACAGCCGCCG
CAACCATGGC CACCG
```

FIG.3

|  | RICE | | | BMS | | |
|---|---|---|---|---|---|---|
|  | EXPT. I | EXPT. II | EXPT. III | EXPT. I | EXPT. II | EXPT. III |
| ALS2-GUS | 3040 | 8337 | 1129 | 3174 |  | 2275 |
|  | 2413 | 5110 | 1033 | 1269 |  | 6117 |
|  | 2847 | 8024 | 1187 | 4145 | 7295 | 3234 |
|  |  |  | 1999 |  | 9419 | 2060 |
|  |  |  |  |  | 8357 | 4018 |
|  |  |  |  |  |  | 3369 |
| AVERAGE | 2767 | 7157 | 1337 | 2863 |  | 3149 |
| STD. DEV. | 321 | 1780 | 446 | 1463 |  | 997 |
| 35S-GUS | 970 |  | 1882 | 348 |  | 334 |
|  | 1175 | 2430 | 1097 | 540 |  | 624 |
|  | 1732 | 3435 | 1235 | 292 | 1021 | 1032 |
|  |  |  | 731 |  | 1228 | 341 |
|  |  |  |  |  | 1125 | 384 |
|  |  |  |  |  |  | 359 |
| AVERAGE | 1292 | 2933 | 1236 | 393 |  | 529 |
| STD. DEV. | 394 |  | 480 | 130 |  | 336 |
| RATIO OF ALS/35S | | | | | | |

FIG. 4A

METHOD OF USING AS A SELECTABLE MARKER A NUCLEIC ACID CONTAINING AHAS PROMOTER USEFUL FOR EXPRESSION OF INTRODUCED GENES IN PLANTS

This application is a division of application Ser. No. 08/303,266, filed Sep. 8, 1994 now U.S. Pat. No. 5,750,866.

FIELD OF THE INVENTION

The present invention is directed to isolated non-coding nucleotide sequences useful as promoters for heterologous gene expression in plants. The present invention is also directed to vectors and plant cells comprising the isolated nucleotide sequences.

BACKGROUND OF THE INVENTION

The Plant Kingdom is divided into two phyla, the Bryophyta and Tracheophyta. The phylum Tracheophyta includes over 266,000 species grouped into four subphyla. Subphylum pteropsida includes Class Angiospermae. This class is divided into two subclasses, the dicotyledons (dicots) and the monocotyledons (monocots).

Since monocots include many of the important grain and feed crops, plant geneticists are keenly interested in being able to produce transgenic monocots. About 50,000 species of monocots are known. These include the lilies, palms, orchids, irises, tulips, sedges, and grasses. The grasses include corn, wheat, rice and all other cereal grains. Unfortunately, monocots have been extremely difficult to genetically engineer so that most of the work with plants has been with dicots.

The dicots are the larger of the two groups, with approximately 200,000 species known. The buttercup, snapdragon, carnation, magnolia, poppy, cabbage, rose, pea, poinsettia, cotton plant, cactus, carrot, blueberry, mint, tomato, sunflower, elm, oak, and maple represent 19 of the 250 families of dicots.

The genetic information within a DNA molecule usually serves as the template for the synthesis of a large number of shorter RNA molecules, most of which in turn serve as templates for the synthesis of specific polypeptide chains. Specific nucleotide segments, (often called promoters), are recognized by RNA polymerase molecules that start RNA synthesis. After transcription of a functional RNA chain is finished, a second class of signals leads to the termination of RNA synthesis and the detachment of RNA polymerase molecules from their respective DNA templates.

Currently, there are a number of common promoters used to drive heterologous gene expression in monocot plants.

David McElroy, et al., (1990) noted that transient expression assays of a construct in which the promoter from the rice actin 1 gene (Act 1) was fused to the bacterial β-glucuronidase gene (GUS) in transformed rice protoplasts showed that the actin promoter drives high levels of gene expression. This expression was about 6-fold greater than that seen with the maize alcohol dehydrogenase 1 gene (Adh1) promoter, and is dependent on the presence of an intact Act1 5' intron.

David McElroy, et al., (1991) noted that optimized vectors for monocot transformation were constructed using either the Cauliflower Mosaic Virus (CaMV) 35S promoter or the Act1 promoter. Transient expression assays were done on both transformed rice and maize protoplasts. Addition of the Act1 intron and optimized GUS translation initiation site to either promoter sequence increased gene expression significantly. It is also noted as an unpublished result that the actin promoter was shown to drive GUS expression in transient assays of wheat, oat, barley and sorghum protoplasts.

Wanggen Zhang, et al., (1991) noted that in situ hybridization studies of transgenic rice plants carrying an Act1-GUS gene fusion showed that the Act1 promoter has a constitutive pattern of expression in both vegetative and reproductive tissue.

Jun Cao, et al., (1992) noted that transgenic rice plants were selected on bialophos following transformation with the bar gene expressed under the control of either the CaMV 35S promoter or the rice Act1 promoter.

Alan H. Christensen, et al., (1992) noted that Maize protoplasts transformed with a maize Ubi-1-CAT gene fusion showed approximately 10-fold higher levels of CAT activity than maize cells transformed with a CaMV-35S-GUS gene fusion in transient expression assays. Northern blot analysis of Ubi-1 and Ubi-2 transcript levels following heat shock of maize seedlings demonstrated that both genes are expressed constitutively at 25C, but are induced following the heat shock.

Seiichi Toki, et al., (1992) noted that stably transformed transgenic rice plants were obtained following electroporation-mediated transformation of the bar gene expressed under the control of the maize Ubi-1 promoter and selection on bialophos. This result demonstrates that the Ubi-1 promoter can be used to drive sufficiently high levels of gene expression in rice to allow for selection and regeneration of fertile, transgenic rice plants.

J. Troy, et al., (1993) noted that stably transformed wheat plants were obtained following bombardment of calli derived from immature embryos with both the bar gene and GUS, each being expressed under the control of the maize Ubi-1 promoter, followed by selection on bialophos. This result demonstrates that the Ubi-1 promoter can be used to drive sufficiently high levels of gene expression in wheat to allow for selection and regeneration of fertile, transgenic plants.

Yuechun Wan, and Peggy G. Lemaux, (1994) noted that stably transformed, fertile barley plants were obtained after microprojectile bombardment of embryonic barley tissues with both the bar gene and GUS, each being expressed under the control of the maize Ubi-1 promoter, followed by selection on bialophos. This result demonstrates that the Ubi-1 promoter can be used to drive sufficiently high levels of gene expression in barley to allow for selection and regeneration of fertile, transgenic plants. An experiment involving bombardment of a small number of plants with either Ubi-bar or CAXV 35S-bar showed no significant difference in the number of transformants obtained.

Junko Kyozuka, et al., (1991) noted that a maize Alh1 promoter-GUS fusion was introduced into rice protoplasts to obtain transgenic rice plants. The GUS activity in the transgenic plants was examined to determine the pattern of GUS expression. The maize Adh1 promoter was found to promote constitutive expression in all parts of the plants examined. As had been previously demonstrated for Adh1 expression in maize, the Adh1-driven GUS expression was induced in roots by anaerobic conditions.

D. I. Last, et al., (1991) noted that when the maize Adh1 promoter was modified by addition of multiple copies of the Anaerobic Responsive element of the maize ADH1 gene and ocs elements from the octopine synthase gene of Agrobacterium tumefaciens (pEmu). In transient expression assays of protoplasts of different moncot species transformed with pEmu-GUS, the best construct, gave 10–50-fold higher levels of expression than the CaMV 35S promoter in wheat, maize, rice, einkorn, and *lolium multiflorum*.

Robert Bower and Robert G. Birch (1992) noted that stable transformants were obtained following transformation of embryogenic callus of sugarcane with the neomycin phosphotransferase gene under the control of the Emu promoter.

D. A. Chamberlain, et al., (1994) noted that the Emu promoter was used to drive the expression of four different selectable marker genes (neomycin phosphotransferase, hygromycin phosphotransferase, phophinothryicin N-acetyltransferase and a mutant acetolactate synthase conferring herbicide resistance) that were transformed into both wheat and rice. Wheat callus and transformed rice plants were obtained after selection of transformants, demonstrating that the promoter can be used to drive expression of selectable marker genes to obtain transformed cereals.

A review of promoter elements used to control foreign gene expression in transgenic cereals has recently been published and is herein incorporated by reference (McElroy and Brettel, Tibtech, Vol. 12, February, 1994).

A number of promoters are currently being used for transformation of dicotyledonous plants. These promoters come from a variety of different sources. One group of commonly used promoters were isolated from *Agrobacterium tumefaciens*, where they function to drive the expression of opine synthase genes carried on the T-DNA segment that is integrated into the plant genome during infection. These promoters include the octopine synthase (ocs) promoter (L. Comai et al., 1985; C. Waldron et al., 1985), the mannopine synthase (mas) promoter (L. Comai et al., 1985; K. E. McBride and K. R. Summerfelt, 1990) and the nopaline synthase (nos) promoter (M. W. Bevan et al., 1983; L. Herrera-Estrella et al., 1983, R. T. Fraley et al., 1983, M. De Block et al., 1984;, R. Hain et al., 1985). These promoters are active in a wide variety of plant tissue.

Several viral promoters are also used to, drive heterologous gene expression in dicots (J. C. Kridl and R. M. Goodman, 1986). The Cauliflower Mosaic Virus 35S promoter is one of the promoters used most often for dicot transformation because it confers high levels of gene expression in almost all tissues (J. Odell et al., 1985; D. W. Ow et al., 1986; D. M. Shah et al., 1986). Modifications of this promoter are also used, including a configuration with two tandem 35S promoters (R. Kay et al.,1987) and the mas-35S promoter (L. Comai et al., 1990), which consists of the mannopine synthase promoter in tandem with the 35S promoter. Both of these promoters drive even higher levels of gene expression than a single copy of the 35S promoter. Other viral promoters that have been used include the Cauliflower Mosaic Virus 19S promoter (J. Paszkowski et al., 1984; E. Balazs et al.) and the 34S promoter from the figwort mosaic virus (M. Sanger et al., 1990).

Studies of AHAS expression in a number of plants indicates that AHAS is expressed in all plant tissues. Gail Schmitt and Bijay K. Singh (1990) noted that enzyme assays performed on various tissues of lima bean demonstrated that AHAS activity was present in all tissues tested, including leaves, stems, roots, flowers, pods and meristems. AHAS activity was found to be fairly constant in the stems, but declined in leaves, roots and meristems with increasing age.

Sharon J. Keeler et al., (1993) noted that tobacco contains two genes encoding acetohydroxyacid synthase, SurA and SurB. Both genes appear to be expressed in all tissue types, with about a four-fold variation in the level of expression in different tissues. Developing organs appear to have the highest levels of expression. In situ hybridization studies demonstrated that the highest levels of expression were consistently observed in metabolically active or rapidly dividing cells. SurB was expressed at higher levels than SurA in all tissues examined.

Therese Ouellet et al., (1992) noted that Brassica species contain multigene families encoding acetohydroxyacid synthase. Four of the five AHAS genes have been identified in *Brassica napus*. RNAse protection assays using gene-specific probes were performed to determine the patterns of expression of the different members of the gene family in various Brassica species. Two of the genes, AHAS1 and AHAS3, were found to be expressed constitutively in all tissues examined. AHAS2 transcripts were detected only in the reproductive organs and extra-embryonic tissue of seeds. Transcripts encoded by the fourth gene, AHAS4, were not detected and it is therefore believed that this represents a pseudogene.

Dale L. Shaner and N. Moorthy Mallipudi (1991) noted that comparison of AHAS activity in young corn leaves and BMS cells grown in suspension culture showed that the activity of the BMS cells per gram fresh weight was approximately 5.8-fold higher than in the leaf samples. Since the BMS cells are actively dividing, this result is consistent with results of previous studies with tobacco and lima bean which demonstrated that younger, actively dividing tissues have more AHAS activity than older tissues.

SUMMARY OF THE INVENTION

AHAS promoters from maize are used to express introduced genes at high levels and in various plant tissues. Promoters from the als1 and als2 genes of maize are cloned and sequenced (FIG. 1, FIG. 2, FIG. 3), and the promoter regions from these genes are then introduced into a plasmid 5' to the reporter gene beta-glucuronidase (GUS). Both promoter fragments are from the XI12 maize line. The als1 promoter fragment is approximately 1400 base pairs long, whereas the als2 promoter fragment contains 819 base pairs. To determine the activity of the AEAS promoters, the chimeric plasmids are then transferred into maize Black Mexican Sweet protoplasts and rice protoplasts for analysis of transient expression levels. For comparison, protoplasts are also transformed with a plasmid with the CaMV 35S promoter driving the GUS reporter gene. The expression of the chimeric plasmids in the maize cells is determined by analyzing the GUS enzyme activity. The activity of the corn als2 promoter was equal to or higher than the activity of the CaXV 35S promoter in both cell types (FIG. 4). FIG. 5 shows the results of beta-glucuronidase assays performed on maize BMS cell lines stably transformed with either pCD221B (als2-GUS-ocs terminator plasmid) or pAC400 (CaMV 35S-GUS-ocs terminator plasmid). Analysis of AHAS mRNA distribution by in situ hybridization of radio-labeled RNA probes to plant tissue shows that the maize AHAS promoters are active in most plant parts (FIG. 6, FIG. 7, FIG. 8).

The activity of the Arabidopsis AHAS promoter is analyzed in Arabidopsis plants that are stably transformed using *Agrobacterium tumefaciens*. The upstream promoter region of the Arabidopsis AHAS gene is fused to the GUS reporter gene, inserted into the binary vector pBIN19 and used to transform Arabidopsis. Analysis of transformed plants shows GUS expression, (indicative of the promoter activity) in most plant parts.

BRIEF DESCRIPTION OF THE DRAWING

FIG. 1 discloses the AHAS promoter sequence ALSI from maize XA17.

FIG. 2 discloses the AHAS promoter sequence ALS2 from maize XA17.

FIG. 3 discloses the AHAS promoter sequence ALS2 from maize XI12.

DETAILED DESCRIPTION OF THE INVENTION

Figure 4B:
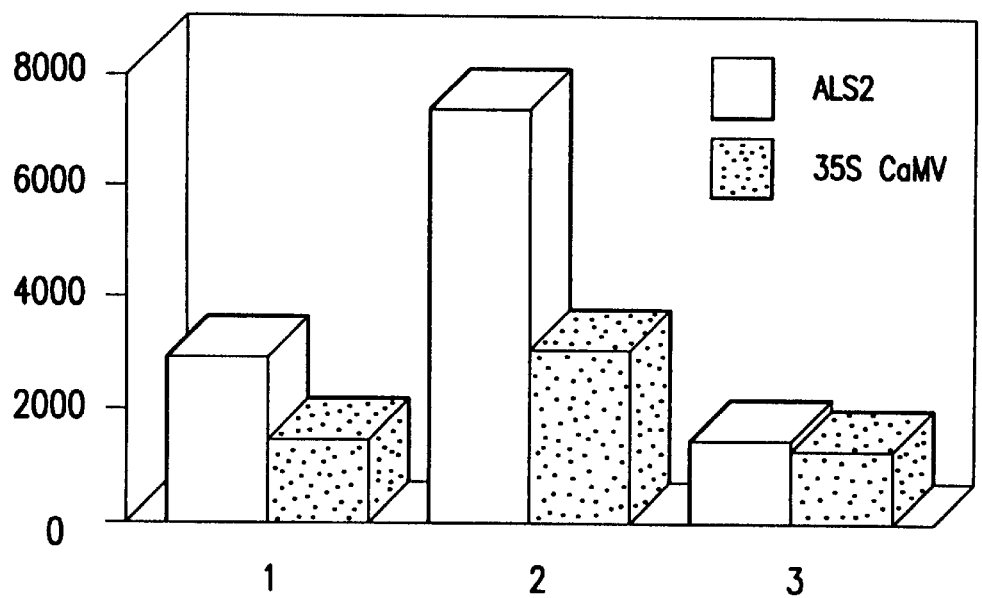
FIG. 4 is a bar graph presenting beta-glucuronidase activity from transient assays of protoplasts of Black Mexican Sweet maize cells or rice suspension cells after transformation with pCD221B (als2-promoter-GUS-ocs terminator plasmid) or AC400 (CAMv 35S-GUS-ocs terminator plasmid). The GUS activity is calculated as pmol/min/mg protein. Results are from three independent experiments.

Scientists are exploring ways to use genetic modification to confer desirable characteristics on plants. Genetic engineering techniques used to improve characteristics such as taste, texture, size, pest-resistance and herbicide-resistance, color, acidity or sweetness of food crops are being explored as a much faster strategy than traditional methods of cross-breeding.

The present invention is directed to AHAS promoters from maize and Arabidopsis and vectors and plant cells comprising these promoters. (For purposes of this application a promoter is defined as a nucleotide sequence found upstream of a gene that acts as a signal for the binding of the RNA polymerase.) The promoter regions from als1 and als2 genes of maize are cloned and sequenced and then introduced into a plasmid 5' to the GUS reporter gene. For purposes of this application a reporter gene is defined as a nucleotide sequence which is fused downstream of the promoter of interest, so that transcripts initiating at the promoter proceed through the reporter gene. Reporter genes encode some easily measurable enzyme activity; for example, in the present invention the expression of chimeric plasmids in maize cells is determined by analyzing the beta-glucuronidase (GUS) enzyme activity.

One skilled in the art should appreciate that AHAS promoters are highly active in many different plant tissues, and can be used to express novel genes in a variety of plants. Novel genes include but are not limited to genes for herbicide resistance, detoxification and resistance towards plant pathogens.

The claimed promoters can be used for heterologous gene expression in monocolyledons, including but not limited to maize, rice, wheat, barley, sorghum, oats, rye and millet. One skilled in the art should also appreciate that the claimed promoters will also drive expression in dicotyledons, although expression of monocot promoters in dicots is expected to be at lower levels than in monocots.

One skilled in the art should appreciate that the maize als2 promoter can be used to drive gene expression in other monocot species. For example, the rice Act1 promoter drives gene expression in maize protoplasts, the maize Emu promoter has been used to select transgenic wheat, barley and rice, and the Arabidopsis AHAS promoter, a dicot promoter, has been used to drive AHAS gene expression in transgenic tobacco and transgenic potato. The claimed maize als2 performs best in maize, but also drives gene expression in another monocot. Based on studies done in maize and other species, this promoter should drive constitutive expression of a gene throughout a plant. The highest levels of expression is seen in either actively dividing or metabolically active tissue.

A variety of different techniques well known by those skilled in the art including, but not limited to, microprojectile bombardment, PEG-mediated transformation, electroporation, and silicon fibers have been used to transform monocot crops. All of these techniques involve the use of DNA vectors for delivery of the nucleotide sequences to be transformed. Vectors suitable for use in the present invention include, but are not limited to, vectors carrying marker genes used for the selection of transgenic material, including genes conferring resistance to hygromycin, kanamycin, bialophos and the imidazolinone and sulfonylurea herbicides.

The following Example serves only to illustrate the invention and is not to be construed as in any way limiting on the invention.

EXAMPLE

Constructs containing the Chimeric CaMV 35S-GUS, als1-GUS and als2-GUS Genes

The efficiency of the als1 and als2 promoters is assessed by measuring GUS activity in maize and rice protoplasts or maize cell lines carrying constructs in which these promoter sequences are fused to the GUS gene. The preparation of the vectors and transformation protpcol is described below.

Plasmid pAC400 is a pUC19-based plasmid containing a fusion of the 418 base pair (bp) EcoRI-XbaI fragment of the CaMV 35S promoter cloned upstream of a 1.7 kb xbaI-PstI fragment containing the GUS gene and a 700 bp PstI-BamHI fragment containing the octopine synthase terminator. The als1 and als2 genes are obtained by screening a genomic library prepared from maize line XI12. An EcoRI-NcoI fragment containing 1.4 kilobase (kb) of sequence upstream from the ATG initiation codon of the als1 gene is subcloned into pAC400 in place of the CaMV 35S promoter to create pCD223B. An 819 bp PstI-NcoI fragment upstream from the ATG of als2 was subcloned in front of the same GUS-ocs terminator fusion in pBluescript® KS-(Stratagene) to create pCD221B. The sequence of the als2 promoter from maize XI12 is presented in FIG. 3.

Transformation and Assay of Protoplasts of Rice and Maize

Protoplasts are isolated from rice (Nortai) or maize (Black Mexican Sweet; BMS) suspension cells and transformed with pAC221B or pAC400 according to the PEG-mediated transformation protocols of L. A. Lyznik et al. (1989) and J. Y. Peng et al. (1990). For transient assays, transformed rice protoplasts are plated on Millipore filters placed on top of medium containing feeder cells and transformed BMS protoplasts are cultured in 3 ml of liquid medium. Two days after transformation, protoplast cultures are collected and extracted with GUS extraction buffer. GUS activity is measured fluorimetrically according to the protocol of R. A. Jefferson (1987).

To recover stable transformants from maize BMS culture, protoplasts are co-transformed with pFF19K (containing the selectable marker gene encoding neomycin phosphotransferase) and pCD221B or pAC400. After transformation, protoplasts are cultured on Millipore filters placed on top of medium containing feeder cells. One week later, the protoplasts cultures are transferred to medium containing feeder cells and 100 mg/1 kanamycin. Protoplasts cultures are transferred to fresh MS medium with 100 mg/1 kanamycin until resistant calluses became visible. Individual kanamycin resistant callus is picked and grown for two to three more weeks in the presence of kanamycin. Kanamycin-resistant callus is stained with X-Gluc or assayed with MUG according to the protocol of R. A. Jefferson (1987) to screen for GUS-positive callus. Callus identified as expressing GUS is ground in extraction buffer and assayed; GUS activity is measured fluorimeterically.

Figure 4C:
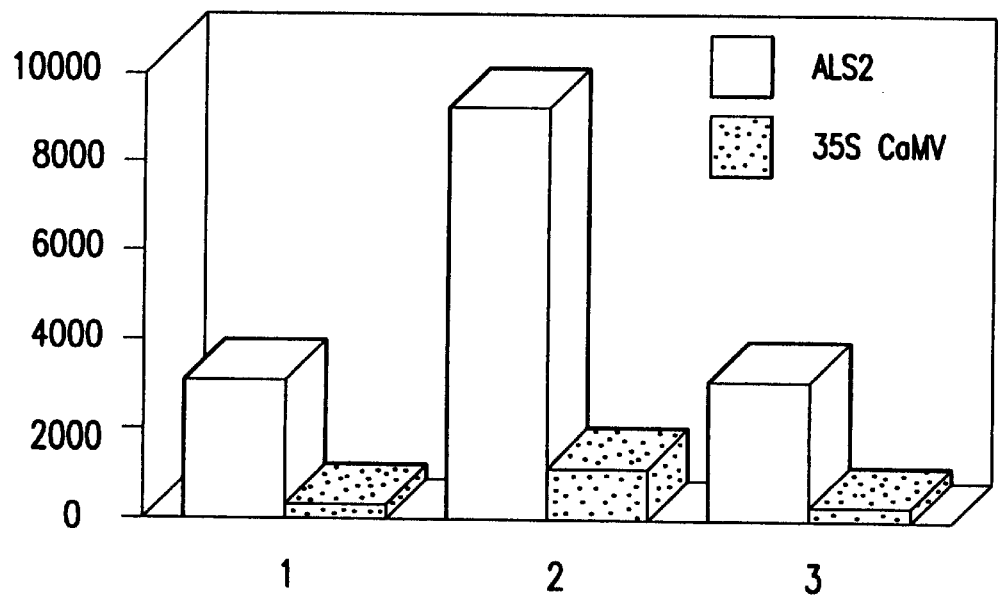
Figure 5:
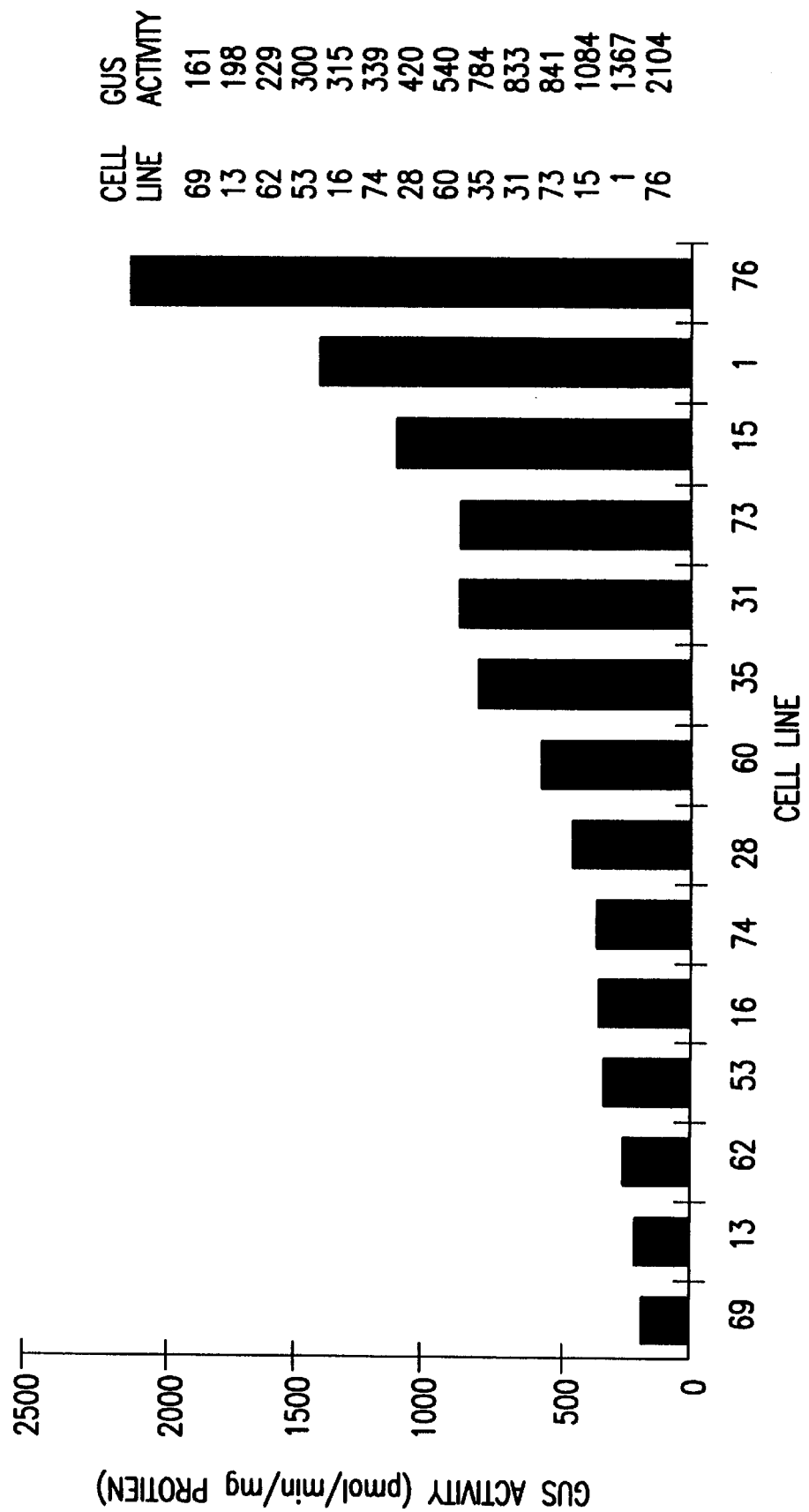
FIG. 5 is a bar graph representing the beta-glucuronidase activity in stably transformed Black Mexican Sweet cell lines after transformation with either pCD221B (als2 promoter-GUS-ocs terminator) or PAC400 (CaMV 35S-GUS-OCS terminator). CK designates untransformed control tissue. The GUS activity is calculated as pmol/min/mg protein.
Figure 6A:
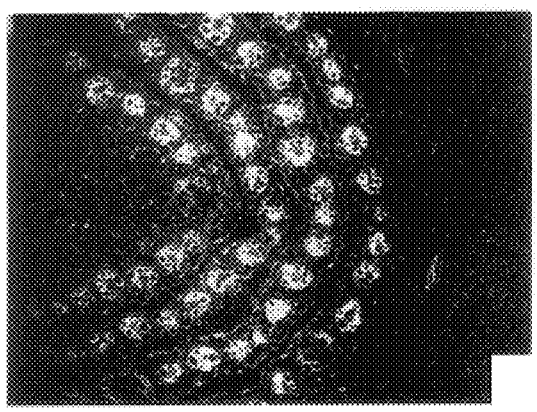
FIG. 6—In situ hybridization studies of leaf whorl from 2 week-old corn seedling using radiolabeled RNA probes. Tissue section were prepared and hybridized to RNA probes encoding either the AHAS sense strand (AHAS−) or the AHAS antisense strand (AHAS+). For a comparison, the SSU (RUBISCO small subunit) sense strand (SSU−) or SSU antisense strand (SSU+) probes were also used. In each case only the antisense strand (+) is expected to hybridize to the mRNA present in the tissue. a) SSU+ probe; b) SSU− probe; c) AHAS+ probe; d) AHAS− probe.
Figure 6B:
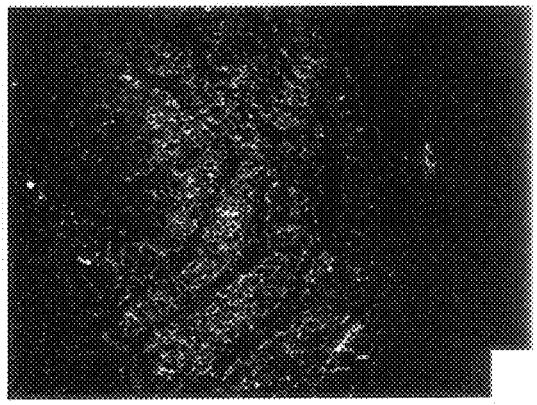
Figure 6C:
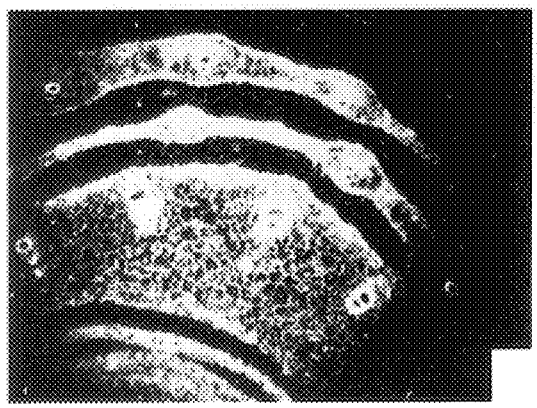
Figure 6D:
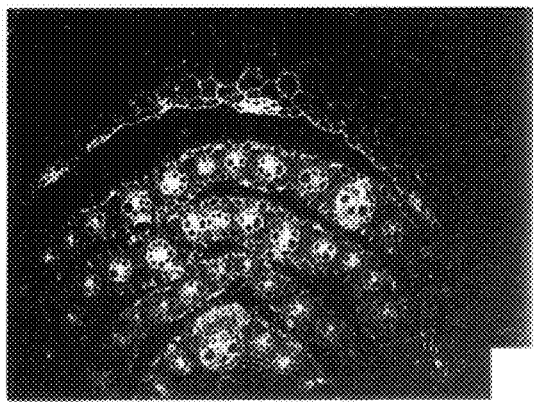
Figure 7A:
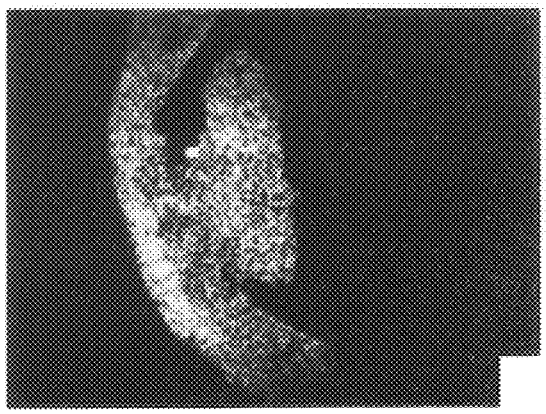
FIG. 7—In situ hybridization studies of corn Kervel 12 days after pollination prepared as described for FIG. 6, a) embryo and suspensor, AHAS+ probe; b) embryo and suspensor, AHAS− probe; c) pericarp, aleurone and endosperm, AHAS− probe; d) pericarp, aleurone and endosperm AHAS+ probe.
Figure 7B:
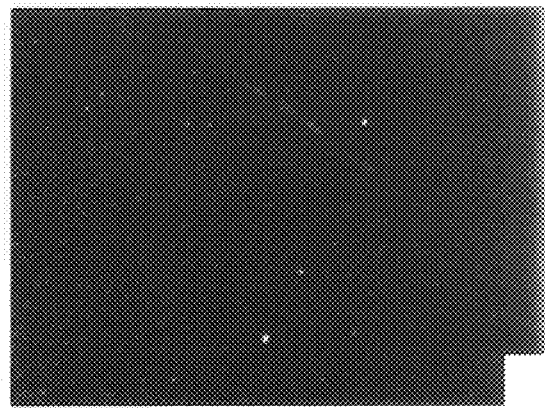
Figure 7C:
Figure 7D:
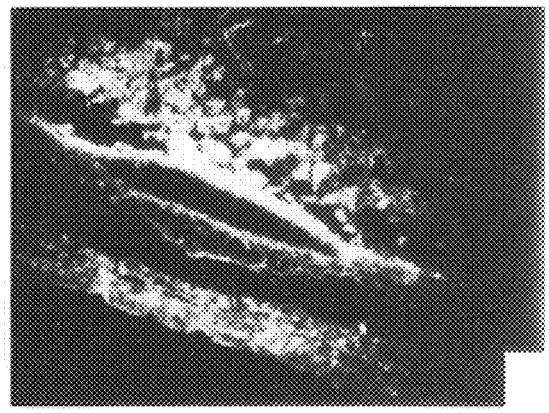
Figure 8A:
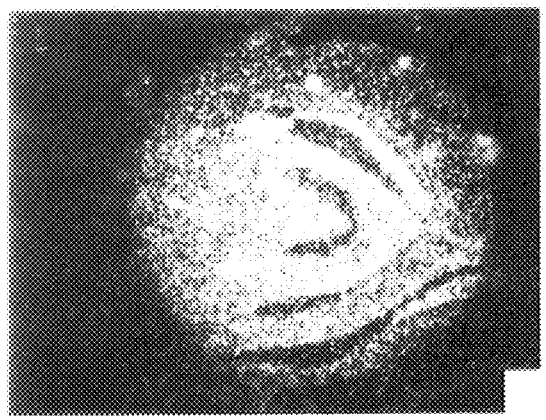
FIG. 8—In situ hybridization studies of apical meristem of young corn plant prepared as described in FIG. 6. a) and b) AHAS+ probe; c) and d) AHAS− probe.
Figure 8B:
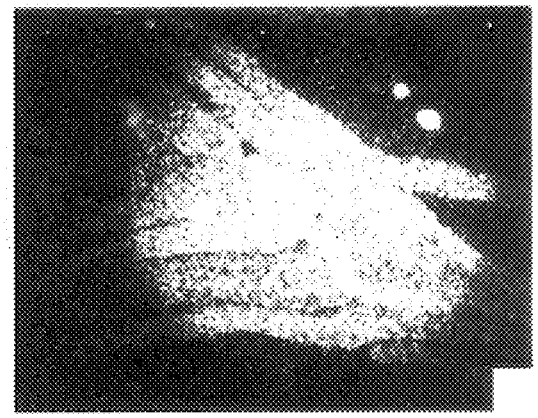
Figure 8C:
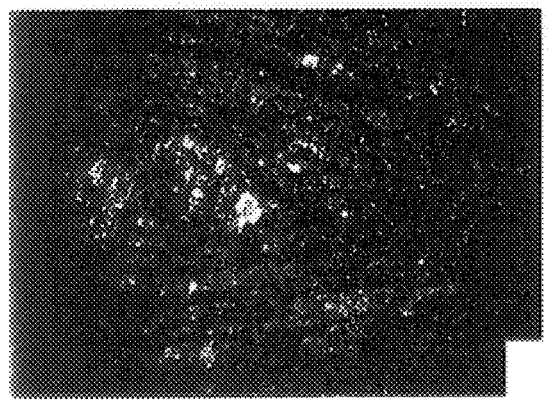
Figure 8D:
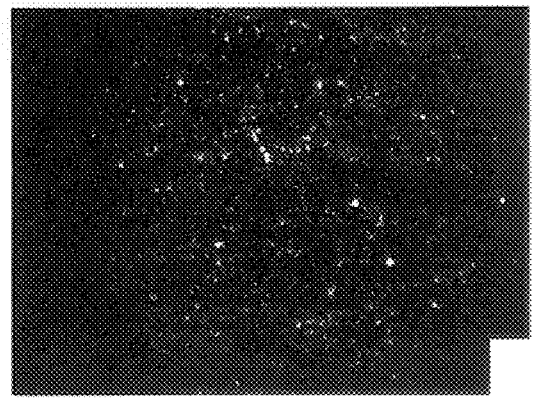

Data from these experiments is presented in FIGS. 4 and 5.

A mutant maize AHAS gene conferring resistance to imidazolinone herbicides and driven by the maize als2 promoter is used as a selectable marker to obtain transgenic callus after transformation of both BMS and A188×B73 cells. This result supports the idea that the als2 promoter drives sufficiently high levels of expression to drive marker gene expression.

Slides are prepared essentially described by J. A. Langdale et al (1988). Tissue is fixed in 4% formaldehyde, dehydrated in ethanol, cleared with xylene and embedded in parafilm. Tissue is sliced into 8–10 μm sections and placed onto slides coated with poly-L-lysine. Paraffin is removed with xylene and tissue is rehydrated by washing in ethanol and rinsing in water. RNA probes are prepared from both strands (+ and −) of a 172 nucleotide (nt) fragment from the als2 encoding region and a 392 nt fragment from the SSU coding region using the Ambion Maxiscript® kit. Slides are hybridized according to the protocol of Meyerowitz et al (1988) at 50° C. overnight in a 1:4 dilution of SPB [100 μl 3M NaCl, 10 mM Tris p.H. 6.8, 50 mM DTA); 400 μl formamide; 200 μl 50% dextran sulphate; 40 μl 10 mg/ml tRNA; 10 μl 1 MDTT; 50 μl 10 mg/ml poly A] with probe denatured in 50% formaldehyde and 10 mM DTT at 80° C. for 30 seconds. Slides are washed 2×15 minutes in Wash Buffer (1×salts, 50% formamide, 10 mM Tris pH 8, 1 mM EDTA and 10 nM DTT) at 50° C., treated with RNase A (20 μg/ml in NTE_ for 30 minutes at 37° C., washed 5× in NTE buffer at 37° C. for a total of 1 hour, washed 2×30 minutes in Wash Buffer at 50° C., dehydrated in ethanol and air dried. Slides are autoradiographed by dipping into emulsion prewarmed to 37° C. in darkroom, drying for 30 minutes to 1 hour and storing in the dark at 4° C. until developing. Slides are developed for 2 minutes, rinsed in water, fixed for at least 5 minutes and rinsed again in water. Tissue is stained with Alcien Blue and destained in ethanol and xylene. After mounting with Permount, tissue is observed using a dark field microscope.

The data from in situ hybridization experiments in FIG. 6–8 shows that the gene is also expressed throughout the maize embryo.

It is possible to evaluate the expression of the AHAS promoter by:

1. constructing an als2-GUS fusion gene and determining the pattern of GUS activity within transgenic corn or rice plants. Previous studies using a maize promoter have demonstrated the feasibility of evaluating maize promoter expression in rice (Junko Kypzuka, et al., 1991). After selection of transgenic plants, histochemical analyses are performed on plant tissues at various stages of development to determine both tissue- and cell type-specificity. This technique is commonly used to evaluate promoter activity in both monocots and dicots.

2. transient expression assays are performed on protoplasts prepared from different plant species following transformation of als2-GUS constructs. This approach is used to evaluate the ability of different promoters to function in heterologous species. Protoplasts are transformed with the construct of interest and incubated to allow the introduced gene to be expressed and the protein to accumulate. Following the incubation, the cells are assayed for the presence of the protein encoded by the transgene to determine the efficiency of the promoter driving transgene expression.

REFERENCES

1. David McElroy et al., (1990) Isolation of an efficient actin promoter for use in rice transformation. The Plant Cell 2: 163–171.
2. David McElroy et al., (1991) Construction of expression vectors based on the rice actin 1 (Act1) 5' region for use in monocot transformation. Mol. Gen Genet. 231: 150–160.
3. Wanggen Zhang et al., (1991) Analysis of the Act1 5' region activity in transgenic rice plants. The plant Cell 3: 1155–1165.
4. Jun Cao et al., (1992) Regeneration of herbicide resistant transgenic rice plants following microprojectile-mediated transformation of suspension culture cells. Plant Cell Reports 11: 586–591.
5. Alan H. Christensen et al., (1992) Maize polyubiquitin genes: structure, thermal perturbation of expression and transcript splicing, and promoter activity following transfer to protoplasts by electroporation. Plant Molecular Biology 18: 675–689.
6. Seiichi Toki et al., (1992) Expression of a maize ubiquitin gene promoter-bar chimeric gene in transgenic rice plants. Plant Physiol. 100: 1503–1507.
7. J. Troy et al., (1993) Rapid production of multiple independent lines of fertile transgenic wheat (*Triticum aestivum*). Plant Physiol. 102: 1077–1084.
8. Yuechun Wan and Peggy G. Lemaux, (1994) Generation of a large number of independently transformed fertile barley plants. Plant Physiol. 104: 37–48.
9. Junko Kyozuka et al., (1991) Anaerobic induction and tissue-specific expression of maize Adh1 promoter in transgenic rice and their progeny. Mol. Gen. Genet. 228: 40–48.
10. D. I. Last et al., (1991) pEmu: an improved promoter for gene expression in cereal cells. Theor. Appl. Genet. 81: 581–588.
11. Robert Bower and Robert G. Birch (1992) Transgenic sugarcane plants via microprojectile bombardment. The Plant Journal 2 (3): 409–416.
12. D. A. Chamberlain et al., (1994) The use of the Emu promoter with antibiotic and herbicide resistance genes for the selection of transgenic wheat callus and rice plants. Aust. J. Plat. Physiol., 21: 95–112.
13. L. Comai et al. (1985) Expression in plants of a mutant aroA gene from *Salmonella typhimurium* confers tolerance to glyphosate. Nature 317: 741–744.

14. C. Waldron et al. (1985) Resistance to hygromycin B: A new marker for plant transformation studies. Plant Mol. Biol. 5: 103–108.
15. Kevin E. McBride and Kristin R. Summerfelt 1990) Improved binary vectors for Agrobacterium-mediated plant transformation. Plant Mol. Biol. 14: 269–276.
16. Michael Bevan et al. (1983) A chimeric antibiotic resistance gene as a selectable marker for plant cell transformation. Nature 304: 184–187.
17. Luis Herrera-Estrella et al. (1983) Expression of chimeric genes transferred into plant cells using Ti-plasmid-derived vector. Nature 304: 209–213.
18. Robert T. Fraley et al. (1983) Expression of bacterial genes in plant cells. P.N.A.S. 80: 4803–4807.
19. Marc De Block et al. (1984) Expression of foreign genes in regenerated plants and in their progeny. EMBO J.3: 1681–1689.
20. R. Hain et al. (1985) Uptake, integration, expression and genetic transmission of a selectable chimeric gene by plant protoplasts. Mol. Gen. Genet. 199: 161–168.
21. J. C. Kridl and Robert M. Goodman (1986) Transcriptional regulatory sequences from plant viruses. Bio Essays 4:4–8.
22. Joan T. Odell et al. (1985) Identification of DNA sequences required for activity of the cauliflower mosaic virus 35S promoter. Nature 313: 810–812.
23. David W. Ow et al (1986) Transient and stable expression of the firefly luciferase gene in plant cells and transgenic plants. Science 234: 856–959.
24. D. M. Shah et al. (1896) Engineering herbicide tolerance in transgenic plants. Science 233: 478–481.
25. Robert Kay et al. (1987) Duplication of CaMV 35S promoter sequences creates a strong enhancer for plant genes. Science 236: 1299–1302.
26. L. Comai et al. (1990) Novel and useful properties of a chimeric plant promoter combining CaMV 35S and MAS elements. Plant Mol. biol. 15: 373–381.
27. J. Pazskowski et al. (1984) Direct gene transfer to plants. EMBOJ. 3: 2717–2722.
28. Ervin Balazs et al. (1985) Chimeric vector construction for higher-plant transformation. Gene 40: 343–348.
29. Margaret Sanger et al. (1990) Characteristics of a strong promoter from figwort mosaic virus: Comparison with the analogous 35S promoter from cauliflower mosaic virus and the regulated mannopine synthase promoter. Plant Mol. Biol. 14: 433–443.
30. Gail Schmidt and Bijay K. Singh (1990) Tissue distribution of acetohydroxyacid synthase activity at various developmental stages of lima bean. Pesticide Sci. 30 (4): 418-419.
31. Sharon J. Keeler et al., (1993) Regulation of tobacco acteolactate synthase gene expression. Plant Physiol. 102:1009–1018.
32. Therese Ouellet et al., (1992) Members of the acetohydroxyacid synthase multigene family of Brassica napus have divergent patterns of expression. The Plant Journal 2: 321–330.
33. Dale L. Shaner and N. Moorthy Mallipudi (1991) Imidazolinone-Acetohydroxyacid synthase interactions. In The Imidazolinone Herbicides ed. Dale L. Shaner and Susan L. O'Connor CRC Press (Boca Raton, Fla.)
34. R. A. Jefferson (1987). Assaying chimeric genes in plants: the GUS gene fusion system. Plant Mol. Biol. Rept 5: 387–405.
35. L. A. Lyznik et al. (1989). Stable transformation of maize protoplasts with gusA and neo genes. Plant Mol biol 13: 151–161.
36. J. Y. Peng et al. (1990). Co-transformation of indica rice protoplasts with neo and gusA genes. Plant Cell Rept 9: 168–172.
37. J. A. Langdale et al., (1988), Cellular pattern of photosynthetic gene expression in developing maize leaves. Gene Dev. 2: 106–115.
38. E. Meyerowitz et al., (1988), In situ hybridization to RNA in plant tissue. Plant Mol. Bio. Rept., 5: 242–250.

We claim:

1. A method of using a nucleic acid construct as a selectable marker wherein the nucleic acid construct comprises an isolated nucleotide sequence which comprises a maize AHAS promoter capable of constitutive expression or a nucleotide sequence selected from the group consisting of SEQ ID NO:1, SEQ ID NO:2, and SEQ ID NO:3, linked to a mutant gene, wherein the mutant gene confers resistance to a selectable material, the method comprising the steps of:

(a) recombinantly transforming a plant material with the nucleic acid construct;

(b) placing the transformed plant material of step (a) on a growth medium comprising the selectable material; and (c) identifying the transformed plant material capable of growth in the presence of the selectable material.

2. The method of claim 1 wherein the mutant gene is an AHAS gene.

3. The method of claim 1 wherein the selectable material is an imidazolinone compound.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 413 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

```
TCTAGAGAAA CTAAACTACT AATAAAAATT ATTTTTAGCA TATTTTAGTA CTGTNGTTTA      60

TATTTNNAAA TGATAAAGTT TAACTAAAAG TGCACCGCTA AACCACCGTA AATCCAAAGA     120

GACCGTAAAT CTCTTCCACG CACTCTGTCG TGTACCAACG TGCTGTGGAA ACGCTCACGT     180

ACCTTTGTGT ATTATGTACG GATTCGGGCA ACGGACATTT CGACGTCGGT TTGCCAGTCC     240
```

-continued

```
NATTCCCATC TGAACCACAC ATCTCTGAAC AAAAGTAGGG GAGGCGCCCG CGTAGCCCCC      300

TTTCCCACAA TCCCACTCCG TGCCAGGTGC CACCCTCCCC AAGCCCTCGC GCCGCTCCGA      360

GACAGCCGCC CGCAACCATG GCCACCGCCG CCACCGCGGC CGCCGCGCTC ACC             413
```

(2) INFORMATION FOR SEQ ID NO:2:

(i) SEQUENCE CHARACTERISTICS:
        (A) LENGTH: 509 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

```
CCGGATTTCC CTGTTGCGGA TTGCGGGTGG CAGCCTGGCA GGTGGGTGCG ACCCCGTTTG       60

GATTCCCTTG TCTGGGCCCC TTGTGTCAGT ACCGTCTGTA CTCCGATGAC ATGCACCGTC      120

GTCCACAGTC AAGTCCAAAA TCTCCCCTCT TTTTTTTAAC GGAACAGTTC AAAACCTCCT      180

TGACGCACGC TGTCGTGTAC CAGCACTCGG TGGACACCAC GTTTGTAATC CAGGCCGACA      240

CGTCGGTCCC ACGTCGACAG GCCCCACCGT CCGGTCTGTA GCGTGTACGT ATTCGGGCGA      300

CGGACGTGTC GTCGTCGTCT TGCGAGTCCC ATTCCCATCA CCATCTGAGC CACACATCCT      360

CTGAACAAAA GCAGGGAGGC CTCCACGCAC ATCCCCCTTT CTCCACTCCG GTCCGTGGCA      420

CCCACCCCAA ACCCTCGCGC CGCCTCCGAG ACAGCCGCCG CAACCATGGC CACCGCCGCC      480

GCCGCGTCTA CCGCGCTCAC TGGCGCCAC                                        509
```

(2) INFORMATION FOR SEQ ID NO:3:

(i) SEQUENCE CHARACTERISTICS:
        (A) LENGTH: 829 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
CTGCAGGTCA ACGGATCACC TATCAACATC CCAGCTAAAA ACAGTAAAAA GGGGGAAAAC       60

GTGGGTGAGT TGAGTCTGTC TTGTGGAAAA AACGTTTTAG TTTCTCCTGG AATTAACAAT      120

AAAAACAGTT GAACAAGATT GACTGTTCCT CCGGGAGGGT TTGGAACATC GTTACAGATG      180

TGAGCGAAAG GTGAGGAAAC AGAGCGGAGG GCTTGGAGGT GACCTCGGTA GTCAGACGCC      240

GGAGTTGAGC TTGATGACGA CACCGTACTG GCGTACCAGG CCTAGTAGTG AACACCGGGC      300

CTGAAGCTGT CGCCGCCGCT GCTCATCTTG TNGGCTGTGC NCGGTGTCCC TGTTGCGGAT      360

TGCGGGTGGC AGCCTGGCAG GTGGGTGCGA CCCGTTTGGA CTCCCTGATC TGGGCCCTTT      420

GTGTCAGTAC CGTCTGTACT CCGATGACAT GCACANCGTC GTCCACAGTC AAGTCCACAA      480

TCTCCCCTCT TTTTTTAACG GAATAGTTNC AAAATCTCCT TGACGCACGC TATCGTGTAC      540

CAGCGCTCAC TGGACACCAC GTTTGTAATC CACGCCGACA CGTCGNTCCC ACGTCGACAG      600

GCCCCACCGT CCGGTCTGTA GCGTGTACGT ATTCGGGCAA CGGACGTGTC GTCGTCGTCT      660

TGCNNNNGTC CCANNNCCCA TCACCATCTG AGCCATCACA TCTCATGCGT GAANAAAAGC      720

AGGGAAGGCC TCTACGCACA TCCCCCTTTC TNNCTNNNNT CCGTGTCCGT GGCACCCAGG      780

GGAAACCCTC GCGCCGCCTC CGAGACAGCC GCCGCAACCA TGGCCACCG                  829
```